US00PP10941P

United States Patent [19]

Bergman

[11] Patent Number: Plant 10,941

[45] Date of Patent: Jun. 8, 1999

[54] HIBISCUS PLANT NAMED 'DESERT WIND'

[75] Inventor: Wendy R. Bergman, Lehigh Acres, Fla.

[73] Assignee: Yoder Brothers, Inc., Barberton, Ohio

[21] Appl. No.: 08/995,355

[22] Filed: Dec. 29, 1997

[51] Int. Cl.[6] ..... A01H 5/00

[52] U.S. Cl. ..... Plt./67.8

[58] Field of Search ..... Plt./67.8

*Primary Examiner*—Howard J. Locker

*Assistant Examiner*—Kent L. Bell

*Attorney, Agent, or Firm*—C. A. Whealy

[57] ABSTRACT

A new and distinct cultivar of Hibiscus plant named 'Desert Wind', characterized by its very dark green leaves; upright and outwardly spreading, uniform and symmetrical plant habit that is appropriate for container production; floriferousness with numerous light orange-colored flowers with red throats; large and flat flowers; good resistance to flower bud abscission; and excellent postproduction longevity.

1 Drawing Sheet

The present invention relates to a new and distinct cultivar of Hibiscus, botanically known as *Hibiscus rosa-sinensis*, and hereinafter referred to by the cultivar name 'Desert Wind'.

The new cultivar is a product of a planned breeding program conducted by the inventor in Alva, Fla. The objective of the breeding program is to create new Hibiscus cultivars having uniform and compact plant habits appropriate for container production, early and uniform flowering, numerous flowers per lateral branch, desirable flower color, resistance to flower bud abscission, and good postproduction longevity.

The new cultivar originated from a cross made by the inventor in Alva, Fla., of the proprietary *Hibiscus rosa-sinensis* selection, designated as code number 399, as the female, or seed, parent with the *Hibiscus rosa-sinensis* cultivar 'Pink Versicolor' (not patented) as the male, or pollen, parent. The cultivar 'Desert Wind' was discovered and selected by the inventor as a flowering plant within the progeny of the stated cross in a controlled environment in Alva, Fla., on Jul. 11, 1994.

Compared to plants of the female parent, the proprietary Hibiscus selection code number 399, plants of the new Hisbiscus are more spreading, have leaves that are not lobed, have better budding uniformity, and have larger flowers. Plants of the new Hibiscus differ in flower color and have narrower petals and flower about one week later than plants of the male parent, the cultivar 'Pink Versicolor'.

Asexual reproduction of the new cultivar by terminal cuttings taken in a controlled environment in Alva, Fla., has shown that the unique features of this new Hibiscus are stable and reproduced true to type in successive generations.

The cultivar 'Desert Wind' has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Desert Wind'. These characteristics in combination distinguish 'Desert Wind' as a new and distinct cultivar:

1. Very dark green shiny leaves.
2. Upright and outwardly spreading, uniform and symmetrical plant habit that is appropriate for container production.
3. Freely flowering, numerous light orange-colored flowers with red throats. Flowers very large and flat.
4. Good resistance to flower bud abscission.
5. Excellent postproduction longevity.

Plants of the new Hibiscus can be compared to plants of the nonpatented cultivar 'Euterpe'. However, in side-by-side comparisons conducted in Alva, Fla., plants of the new cultivar differ from plants of the cultivar 'Euterpe' in the following characteristics:

1. Plants of the new Hibiscus are more compact and more outwardly spreading than plants of the cultivar 'Euterpe'.
2. Leaves of plants of the new Hibiscus are not lobed whereas leaves of plants of the cultivar 'Euterpe' are lobed.
3. Plants of the new Hibiscus are more floriferous than plants of the cultivar 'Euterpe'.
4. Plants of the new Hibiscus have better budding uniformity than plants of the cultivar 'Euterpe'.
5. Plants of the new Hibiscus are much more resistant to flower bud abscission than plants of the cultivar 'Euterpe'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a top perspective view of typical plant of 'Desert Wind'.

The photograph at the bottom of the sheet comprises a close-up view of a typical flower of 'Desert Wind'. Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color references are made to The Royal Horticultural Society Colour Chart except where general terms of ordinary dictionary significance are used.

Botanical classification: *Hibiscus rosa-sinensis* cultivar 'Desert Wind'.

Parentage:

*Female or seed parent.*—*Hibiscus rosa-sinensis* proprietary selection designated as code number 399.

*Male or pollen parent.*—*Hibiscus rosa-sinensis* cultivar 'Pink Versicolor', not patented.

Propagation:

*Type*.—By terminal cuttings.

*Time to initiate roots*.—About 10 days at temperatures of 24° C.

*Times to develop roots*.—About 28 days at temperature of 24° C.

*Rooting habit*.—Moderately vigorous, thick and well-branched.

Plant description:

*Plant form and growth habit*.—Perennial, evergreen, upright and outwardly spreading, inverted triangle, uniform and symmetrical plant habit. Moderate vigor.

*Branching habit*.—Freely branching, usually about six lateral branches develop after removal of terminal apex.

*Plant height, soil level to top of flowers*.—About 43 cm.

*Plant diameter, area of spread*.—About 50 cm.

*Lateral branch description*.—Length: About 38 cm. Diameter: About 8 mm. Texture: Immature, smooth; woody with age.

*Color*.—Immature: 144A/146A. Mature: Dark brown.

Foliage description:

*Arrangement*.—Alternate, single.

*Length*.—About 9.5 cm.

*Width*.—About 7 cm.

*Shape*.—Ovate.

*Apex*.—Acute to acuminate.

*Base*.—Obtuse.

*Margin*.—Entire to crenate.

*Aspect*.—Undulate.

*Texture*.—Glabrous and very shiny on both surfaces.

*Color*.—Young foliage, upper surface: Brighter and darker than 146A. Young foliage, lower surface: Greener than 146A. Mature foliage, upper surface: Very dark green, much darker than 147A. Mature foliage, lower surface: Darker than 147B.

*Petiole*.—Length: About 3.75 cm. Diameter: About 4 mm. Texture: Smooth or with very fine pubescence on upper surface. Color: Upper, 147A; lower, 146A.

Flower description:

*Natural flowering season*.—Usually spring and summer or during periods of warm weather.

*Flower arrangement*.—Flowers arranged singly at terminal leaf axils. Freely flowering with usually about five flower buds and/or open flowers per terminal apex. Flowers face upright.

*Flower appearance*.—Very large and flat star-shaped single flowers. Light orange-colored petals with red throat. Flowers are open for about one day before closing. Flowers persistent.

*Flower diameter*.—About 14.5 cm.

*Flower bud* (*just before showing color*).—Rate of opening: About one day depending on temperatures. Length: About 2.4 cm. Diameter: About 1 cm. Shape: Columnar, oblong.

*Petals*.—Texture: Crepe, smooth. Arrangement: Corolla consists of five petals that overlap. Shape: Spatulate with rounded apex. Margin: Entire, slightly ruffled. Length: About 9 cm. Width: About 7 cm. Color: Opening: 23A. Upper surface: Close to 26A/26B. Lower surface: 37A/37B to close to 29A/29B; veins, pinkish. Yellowish orange at right edges of petals. Throat: Red, shiny, 45A/46A.

*Sepals*.—Appearance: Six sepals fused into a star-shaped calyx. Shape: Linear. Texture: Smooth. Color, outer surface: 146A.

*Peduncles*.—Length: About 5 cm. Diameter: About 3.5 mm at apex. Angle: Upright. Strength: Strong, rigid. Color: 146A.

*Reproductive organs*.—Androecium: Stamen number: Numerous. Stamen length: About 7.5 mm. Anther shape: Globular. Anther size: About 1 mm. Amount of pollen: Abundant. Pollen color: 21A. Gynoecium: Pistil length: About 9 cm. Style color: Apex: White. Base: 46A to 47A. Stigma number: Five. Stigma shape: Round. Stigma diameter: Large, about 4 mm. Stigma color: Golden orange, 23A. Ovary color: Light green, 154A/154B.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Desert Wind', as illustrated and described.

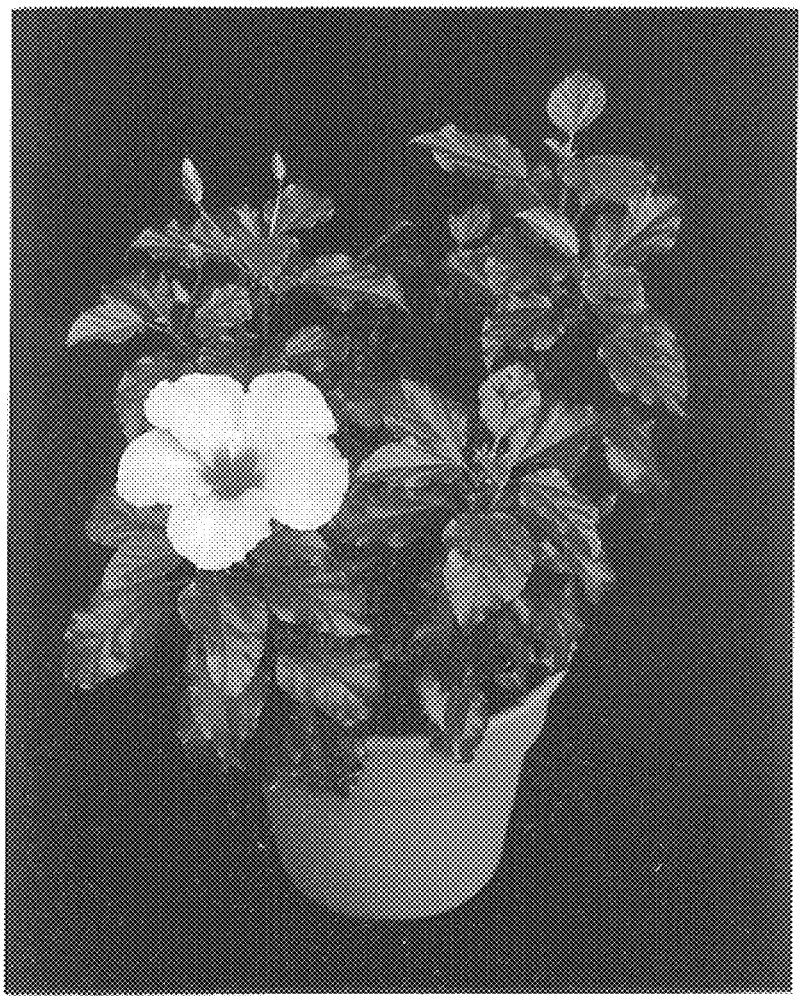
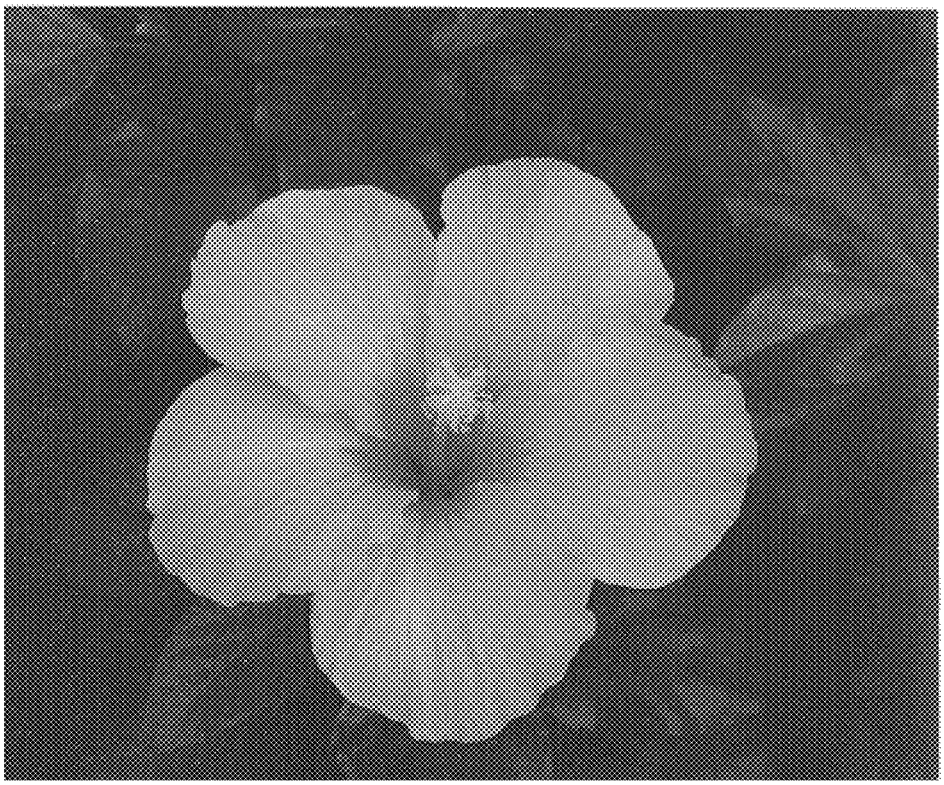

* * * * *